United States Patent [19]
Maier et al.

[11] Patent Number: 5,746,995
[45] Date of Patent: May 5, 1998

[54] DTPA DERIVATIVES SUBSTITUTED IN A NOVEL WAY, THEIR METAL COMPLEXES, AND THEIR USE IN DIAGNOSIS AND THERAPY

[75] Inventors: Franz-Karl Maier; Michael Bauer; Werner Krause; Ulrich Speck; Gabriele Schuhmann-Giampieri, all of Berlin, Germany; Andreas Muhler, Wayne, N.J.; Thomas Balzer; Wolf-Rudiger Press, both of Berlin, Germany

[73] Assignee: Schering Aktiengesellschaft, Berlin, Germany

[21] Appl. No.: 565,025

[22] Filed: Nov. 30, 1995

Related U.S. Application Data

[63] Continuation-in-part of Ser. No. 387,408, Feb. 13, 1995, which is a continuation-in-part of Ser. No. 35,186, Nov. 30, 1994, abandoned.

[51] Int. Cl.$^6$ .......................... A61B 5/055; A61K 49/04
[52] U.S. Cl. ................. 424/1.65; 424/9.361; 424/9.364; 424/9.42; 534/10; 534/13; 534/16; 514/184; 514/492; 514/502; 514/836; 556/50; 556/55; 556/63; 556/77; 556/105; 556/116; 556/134; 556/148; 436/173
[58] Field of Search .................. 424/9.363, 9.364, 424/9.365, 9.361, 9.42, 1.65; 514/184, 492, 502, 836; 436/173; 128/653.4, 654; 534/16, 10, 13; 556/50, 55, 63, 77, 105, 116, 134, 148

[56] References Cited

U.S. PATENT DOCUMENTS

| | | | |
|---|---|---|---|
| 3,994,966 | 11/1976 | Sundberg et al. | 260/518 R |
| 4,339,426 | 7/1982 | Meares et al. | 424/1 |
| 4,622,420 | 11/1986 | Meares et al. | 562/443 |
| 4,647,447 | 3/1987 | Gries et al. | 424/9 |
| 4,652,519 | 3/1987 | Warshawsky et al. | 435/7 |
| 4,672,028 | 6/1987 | Olson | 435/5 |
| 4,824,986 | 4/1989 | Gansow | 558/17 |
| 4,880,008 | 11/1989 | Lauffer | 128/654 |
| 4,899,755 | 2/1990 | Lauffer et al. | 128/654 |
| 4,916,246 | 4/1990 | Felder et al. | 556/1 |
| 5,057,302 | 10/1991 | Johnson et al. | 424/1.1 |
| 5,101,041 | 3/1992 | Troutner et al. | 548/518 |
| 5,137,711 | 8/1992 | Weber et al. | 424/9 |
| 5,198,208 | 3/1993 | Berg et al. | 424/1.1 |
| 5,250,285 | 10/1993 | Lauffer et al. | 424/9 |
| 5,316,756 | 5/1994 | Gries et al. | 424/9 |
| 5,318,771 | 6/1994 | Lauffer et al. | 424/9 |
| 5,399,340 | 3/1995 | Radüchel et al. | 424/9 |
| 5,419,894 | 5/1995 | Gries et al. | 424/1.65 |
| 5,482,700 | 1/1996 | Deutsch et al. | 424/9.364 |

FOREIGN PATENT DOCUMENTS

| | | |
|---|---|---|
| 0 165 716 | 12/1985 | European Pat. Off. . |
| 0 230 893 | 8/1987 | European Pat. Off. . |
| 0 299 795 | 1/1989 | European Pat. Off. . |
| 0 305 320 | 3/1989 | European Pat. Off. . |
| 0 315 220 | 5/1989 | European Pat. Off. . |
| 0 405 704 | 1/1991 | European Pat. Off. . |
| 1374979 | 11/1974 | United Kingdom . |
| 95/15319 | 6/1985 | WIPO . |
| 88/07521 | 10/1988 | WIPO . |
| 89/05802 | 6/1989 | WIPO . |
| 94/27644 | 12/1994 | WIPO . |

OTHER PUBLICATIONS

Havron et al. "Heavy Metal Particulate Contrast Materials for Computed Tomography of the Liver," Journal of Computer Assisted Tomography, 4(5):642–648 (Oct. 1980).

Seltzer et al. "Hepatic Contrast Agents for Computed Tomography: High Atomic Number Particulate Material," Journal of Computer Assisted Tomography, 5(3):370–374 (Jun. 1981).

Bloem et al., "Gd–DTPA as a Contrast Agent in CT," Radiology, 171(2):578–579 (May 1989).

Zwicker et al., "Kontrastgebung von Jod, Gadolinium und Ytterbium in der CT," Fortschr. Röntgenstr., 158(3):255–259 (1993) (Abstract Only).

Schmitz et al., "Evaluation of Gadobutrol in a Rabbit Model as a New Lanthanide Contrast Agent for Computed Tomography," Investigative Radiology, 30(11):644–649 (Nov. 1995).

Unger et al., "Utterbium–DTPA –A Potential Intravascular Contrast Agent," Investigative Radiology, 21(10):802–807 (Oct. 1986).

*Primary Examiner*—Gary E. Hollinden
*Attorney, Agent, or Firm*—Millen, White, Zelano, & Branigan, P.C.

[57] ABSTRACT

The invention relates to new diethylenetriaminepentaacetic acid derivatives, their complexes and complex salts, that contain an element of atomic numbers 20–32, 39–51 or 57–83, pharmaceutical agents that contain these compounds and their use as contrast media and antidotes.

29 Claims, No Drawings

DTPA DERIVATIVES SUBSTITUTED IN A NOVEL WAY, THEIR METAL COMPLEXES, AND THEIR USE IN DIAGNOSIS AND THERAPY

This application is a continuation-in-part of U.S. application Ser. No. 08/387,408, filed Feb. 13, 1995, which is a continuation-in-part of U.S. application Ser. No. 08/351,086, filed Nov. 30, 1994 abandoned. U.S. application Ser. No. 08/487,094, filed Jun. 6, 1995, is also a continuation-in-part application of U.S. application Ser. No. 08/387,408. U.S. application Ser. No.08/480,566, filed Jun. 7, 1995, is a divisional application of Serial No. 08/487,094 U.S. Pat. No. 5,672,335. The entirety of each of the above-mentioned applications is hereby incorporated by reference.

SUMMARY OF THE INVENTION

The invention relates to DTPA (diethylenetriaminepentaacetic acid) derivatives substituted in a novel way and their metal complexes, pharmaceutical agents that contain these complexes and their use in diagnosis and therapy.

Contrast media are indispensable additives in modern diagnosis; thus many diseases could not be diagnosed without the use of contrast media. Contrast media are used in all areas of diagnosis, such as, e.g., diagnostic radiology, radiodiagnosis or ultrasound diagnosis or magnetic resonance imaging (MRI or NMR imaging).

The selection of the method preferred in each case depends, i.a., on the diagnostic problem, but is also determined by the choice of apparatus available in each case to the physician. Thus, because of the considerable technical expenditure and associated high cost, in particular magnetic resonance imaging has not yet found the wide use of other methods, such as, e.g., methods of diagnostic radiology.

The selection of the suitable contrast medium also varies on the basis of the respective problem. Thus, the suitability of the contrast medium for a specific object is determined last but not least by its concentration and distribution behavior in the organism.

Although great progress has been achieved both on the equipment side and on the contrast medium side, solutions satisfactory for all problems are not yet available.

Thus, suitable contrast media do not exist for all indications for the various imaging processes. In particular, until now, no suitable X-ray contrast medium for liver diagnosis has been available.

In diagnostic radiology, basically contrast media based on triiodobenzene have been able to gain acceptance, since these compounds exhibit a high X-ray opacity, a low general and local toxicity and are very readily water-soluble.

Such compounds are described, e.g., in EP 0 105 752 and EP 0 015 867. But, the latter show insufficient concentration in the liver for a diagnostic X-ray imaging.

The radio-opaque effect of an X-ray contrast medium is basically dependent on the size of the mass attenuation coefficient of the elements, contained in the compound, in the diagnostic range of radiation. In addition to iodine-containing compounds, complexes of metals of higher atomic numbers are also suitable as X-ray contrast media. Physiologically compatible complex compounds of these metals are already widely used in the field of NMR diagnosis. In general, these are metal complexes, as they are described, e.g., in EP 0 071 564.

WO 93/16375 describes metal complexes, which are linked by amide bonds to iodine-substituted aromatic compounds. These compounds are intended to allow both NMR and X-ray investigations to be performed with only one administration of contrast medium. A combination of the two imaging processes is advantageous in many cases for a differentiated visualization and a reliable determination of certain diseases. These compounds are to be suitable especially for angiography. As the reprocessing of the production samples reveals, however, the compounds show insufficient concentration in the area of the liver for X-ray investigations.

An object of the invention therefore is to make available very well-tolerated and water-soluble contrast media, as well as a process for their production that is as simple as possible, which are suitable for diagnostic radiology, NMR diagnosis and radiodiagnosis or radiotherapy—especially for diagnostic radiology of the liver.

Upon further study of the specification and appended claims, further objects and advantages of this invention will become apparent to those skilled in the art.

These objects are achieved by the substances, agents and methods described below.

It has been found that metal complexes of general formula I

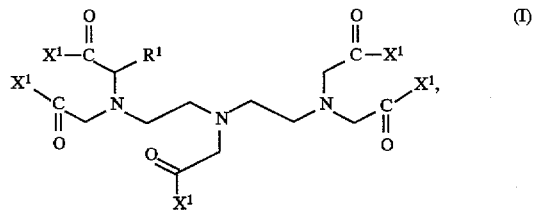

in which
R$^1$ stands for a radical of formula Ia
in which

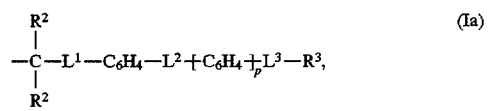

p stands for number 0 or 1,

R$^2$, independently of one another, in each case stands for a hydrogen atom or a branched or unbranched, saturated or unsaturated C$_1$–C$_6$ hydrocarbon radical, R$^3$ stands for a hydrogen atom or a branched or unbranched, saturated or unsaturated C$_1$–C$_6$ hydrocarbon radical or a carboxyl group, L$^1$ stands for a direct bond or a C$_1$–C$_4$ alkylene chain, L$^2$ and L$^3$, respectively independently of one another, each stand for a direct bond, an oxygen atom, a sulfur atom or a C$_1$–C$_{10}$ alkylene chain, which optionally is interrupted by one to three oxygen atoms and/or one to three sulfur atoms, and two or more heteroatoms must not be directly bonded with one another, and X$^1$, independently of one another, in each case stands for a group O—X$^2$ or N(R$^4$)R$^5$, R$^4$ and R$^5$, independently of one another, in each case stand for a hydrogen atom, C$_1$–C$_6$ alkyl, or for a group R$^1$ or R$^4$ and R$^5$ together, with inclusion of the common amide nitrogen atom, form a four- to eight-membered ring, which can in addition, optionally, contain up to two additional oxygen atoms and/or up to two carbonyl or sulfonyl groups, and $X^2$, independently of one another, in each case stands for a hydrogen atom or a metal ion equivalent of an element of atomic numbers 20–32, 39–51 or 57–83, as well as salts thereof with the physiologically compatible inorganic and/or organic cations, for example, for charge equalization are very well suited for the production of contrast media for diagnostic radiology and/or NMR diagnosis and/or radiodiagnosis, preferably contrast media for diagnostic radiology, especially for diagnostic radiology of the liver, the bile ducts and the gallbladder.

The invention therefore relates to the compounds of general formula I.

Compounds of general formula I in which all occurring radicals $X^2$ have the meaning of hydrogen atoms are referred to as complexing agents or as ligands. Compounds of general formula I, in which at least one of the contained heteroatoms (oxygen, nitrogen or sulfur) is bound in a coordinated manner to a metal atom, are referred to as complexes.

Compounds of general formula I, in which at least two of the contained heteroatoms (oxygen, nitrogen or sulfur) are bound in a coordinated manner to the same metal atom, are referred to as chelate complexes.

If the metal complex according to the invention is intended for the production of agents for diagnostic radiology, the central ion must be derived from an element of a higher atomic number to achieve a sufficient absorption of the x rays. It has been found that elements of atomic numbers 57–83 are especially suitable for this purpose. Quite especially suitable are complexes of the elements lanthanum, gadolinium, terbium, dysprosium, holmium, erbium, ytterbium, lutetium, bismuth, lead and hafnium.

If the metal complex according to the invention is intended for the production of agents for NMR diagnosis, the central ion must be paramagnetic. It has been found that for this purpose, especially the chromium(III), iron(II), cobalt(II), nickel(II), copper(II), praseodymium(III), neodymium(III), samarium(III) and the ytterbium(III) ions are suitable. Especially preferred are complexes of the gadolinium(III), terbium(III), dysprosium(III), holmium (III), erbium(III) iron(III) and manganese(II) ions.

If the metal complex according to the invention is intended for the production of agents for nuclear medicine, the central ion must be radioactive. Suitable are, for example, the radioisotopes of the elements copper, cobalt, gallium, germanium, yttrium, strontium, technetium, indium, ytterbium, gadolinium, samarium, silver, gold, rhenium, bismuth and iridium. Preferred radioisotopes are gallium-67, indium-111 and technetium-99 m.

Suitable $C_1$–$C_6$ hydrocarbon radicals for $R^2$ and $R^3$ include methyl, ethyl, isopropyl, propyl, butyl, vinyl, phenyl and cyclohexyl.

The compounds according to the invention can contain, as groups of formula —C(=O)$X^1$, carboxylates (—CO$_2X^2$) or carboxylic acid amides (—C(=O)N($R^4$)$R^5$). Radicals $R^4$ and $R^5$, independently of one another, can be hydrogen atoms or radicals of formula $R^1$. Suitable are, for example, compounds in which one or two carboxylic acid groups that are present in the molecule are present as alkylamides (for example, methyl-, ethyl-, propyl- or butylamides). Also suitable are compounds in which one or two carboxylic acid groups that are present in the molecule are present as benzylamides or their derivatives, for example, methoxybenzylamide, ethoxybenzylamide, propoxybenzylamide, butoxybenzylamide, benzyloxybenzylamide, methylbenzylamide, ethylbenzylamide, propylbenzylamide, butylbenzylamide or benzylbenzylamide.

Radicals $R^4$ and $R^5$ can also together form, for example, a $C_3$–$C_7$ alkylene chain which together with inclusion of the amide nitrogen atom, forms a four- to eight-membered ring, which can contain zero to two additional oxygen atoms and/or zero to two additional carbonyl or sulfonyl groups. If $R^4$ and $R^5$ together stand for a ring system, the morpholine ring or the S,S-dioxothiomorpholine ring are preferred.

As radicals $R^1$ of general formula I, lipophilic radicals that are described by Formula Ia are used. Particularly, those radicals that contain aromatic groups or are interrupted by aromatic groups exhibit advantageous properties. Radicals $R^1$can also contain heteroatoms, such as nitrogen, oxygen or sulfur, in which two heteroatoms are not connected with one another. In particular, substituted benzyl radicals can be used as radical $R^1$, such as, for example, methoxybenzyl, ethoxybenzyl, propoxybenzyl, butoxybenzyl, pentoxybenzyl, benzyloxybenzyl, methylbenzyl, ethylbenzyl, propylbenzyl, butylbenzyl, pentylbenzyl and benzylbenzyl radicals. Especially suitable is the butylbenzyl radical. Radicals $R^1$ can also contain several heteroatoms, such as, for example, (ethoxy)ethoxybenzyl, 2-(2-ethoxyethoxy)-ethoxybenzyl, 2-(methoxy)ethoxybenzyl and ((ethoxy)ethoxy)methoxybenzyl radicals; preferred is the ethoxybenzyl radical. The benzyl radicals can be substituted in 2-, 3- or 4-position, i.e., in ortho, meta or para position. Substituents in ortho and para position are preferred in this case, quite especially preferred are radicals in para position.

It is often the case that the complexing agent exhibits more acid functions than the complexed metal has positive elementary charges. Thus, for example, the 3,6,9-triaza-3,6, 9-tris-(carboxymethyl)-2-(4-ethoxybenzyl)-undecanedioic acid described in Example 1 has five acid groups, while the dysprosium is present in dysprosium oxide (Dy$_2O_3$) in oxidation stage +III. In the case of complexing, thus only three of the five protons of the acid are neutralized. A complex which contains two protons that can be dissociated, an acid complex, is thus formed. In aqueous solution, two protons and one dianion —formed from the metal and the complexing agent—are thus present. For many purposes, it is advantageous to exchange the protons for other physiologically compatible cations (neutralization), so that a salt is formed. As physiologically compatible cations, sodium$^+$, calcium$^{2+}$, magnesium$^{2+}$ and zinc$^{2+}$ as well as cations of organic bases, such as meglumine, glucosamine, arginine, ornithine, lysine and ethanolamine, can be mentioned as examples.

Production of the Complexes According to the Invention

Production of the complexes according to the invention can take place, for example, in the way disclosed in patent specifications EP 71564, EP 130934 and DE-OS 3401052, by a metal oxide or a metal salt (for example, a chloride, nitrate, acetate, carbonate or sulfate) of the element of atomic numbers 20–32, 39–51 or 57–83 being dissolved or suspended in water and/or another polar solvent (such as methanol, ethanol, isopropanol or N,N-dimethylformamide) and reacted with a solution or suspension of the equivalent amount of a complexing agent of general formula II

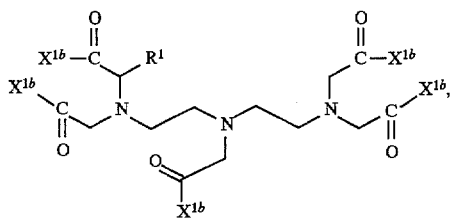

(II)

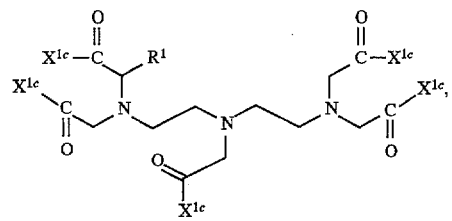

(III)

in which

R¹ has the above-mentioned meanings, $X^{1b}$, independently of one another, in each case stands for a group HO or $N(R^4)R^5$, with $R^4$ and $R^5$ having the above-mentioned meanings, and then, if desired, existing acid hydrogen atoms of acid groups can be substituted by cations of inorganic and/or organic bases or amino acids.

In this case, the neutralization takes place with the help of inorganic bases (e.g., hydroxides, carbonates or bicarbonates) of, e.g., sodium, calcium or lithium and/or organic bases, such as, i.a., primary, secondary and tertiary amines, such as, e.g., ethanolamine, glucamine, N-methylglucamine and N,N-dimethylglucamine, as well as basic amino acids, such as, e.g., lysine, arginine and ornithine.

For the production of neutral complex salts, enough of the desired bases can be added, for example, to the acid complex salts in aqueous solution or suspension so that the neutral point is reached. The obtained solution can then be evaporated to dryness in a vacuum. Often, it is advantageous to precipitate the formed neutral salts by the addition of water-miscible solvents, such as, e.g., lower alcohols (methanol, ethanol, isopropanol, etc.), lower ketones (acetone, etc.), polar ethers (tetrahydrofuran, dioxane, 1,2-dimethoxyethane, etc.) and thus to obtain easily isolated and readily purified crystallizates. It has proven especially advantageous to add the desired base as early as during the complexing of the reaction mixture and thus to save a process step.

If the acid complexes contain several free acid groups, it is often suitable to produce neutral mixed salts, which contain both inorganic and organic cations as counterions.

This can happen, for example, by reacting the complexing agents in aqueous suspension or solution with the oxide or salt of the desired element and half of the amount of an organic base required for neutralization. The formed complex salt can then be isolated, optionally purified and then mixed with the required amount of inorganic base for complete neutralization. The sequence of the addition of bases can also be reversed.

Another possibility to arrive at neutral complex compounds involves converting the remaining acid groups, as described, e.g., in EP 0450742, completely or partially to amides.

If the agents according to the invention are to contain radioisotopes, the production of the complexes from the complexing agents can take place according to the methods described in "Radiotracers for Medical Applications,"Vol. I, CRC Press, Boca Raton, Fla.

Production of the Complexing Agents According to the Invention

Production of the compounds of general formula I generally takes place by cleavage of the acid protective groups of compounds of general formula III in which R¹ has the above-mentioned meanings, $X^{1c}$, independently of one another, in each case stands for a group ZO or $N(R^4)R^5$, with $R^4$ and $R^5$ having the above-mentioned meanings, in which Z has the meaning of an acid protective group.

The acid protective groups and process for their cleavage are well known to one skilled in the art or can be found in relevant literature (e.g.: Protective Groups in Organic Syntheses, Second Edition, T. W. Greene and P. G. M. Wuts, John Wiley & Sons, Inc., New York, 1991).

Possibilities for the production of the compounds of general formula III are known to one skilled in the art. Actual embodiments of production processes are described in the examples. One skilled in this field has extensive technical knowledge as to how these processes can be modified to be able to obtain the compounds desired in each case.

Additional information about reaction processes and reaction conditions is published in the following publications:

Synthesis of ethers, in particular phenolic ethers:

Houben-Weyl, Band VI/3, Teil A, Georg Thieme Verlag, Stuttgart, 1965

Synthesis of amines and amino acid derivatives:

Houben-Weyl, Band XI/1, Georg Thieme Verlag, Stuttgart, 1957, Houben-Weyl, Band XI/2, George Thieme Verlag, Stuttgart, 1958

Synthesis of Alkyl halides:

Houben-Weyl, Band V/3, Georg Thieme Verlag, Stuttgart, 1962, Houben-Weyl, Band V/4, Georg Thieme Verlag, Stuttgart, 1960

Synthesis of carboxylic acids and derivatives thereof:

Houben-Weyl, Band VIII, Georg Thieme Verlag, Stuttgart, 1952

Synthesis of sulfonic acid derivatives:

Houben-Weyl, Band IX, Georg Thieme Verlag, Stuttgart, 1955

Reductive amination:

C. F. Lane, Synthesis 135 (1975)

Synthesis of DTPA derivatives:

M. A. Williams, H. Rapoport, J. Org. Chem., 58, 1151 (1993)

Pharmaceutical Agents

Another object of the invention are agents, which contain at least one of the compounds according to the invention as well as a process for the production of these agents, which is characterized in that the chelate complex is dissolved in water and put into a form that is suitable for enteral or parenteral administration with the additives and stabilizers usual in galenicals, so that the chelate complex is present in a concentration of preferably about 1 to 1500 mmol/l, especially in a concentration of about 10 to 1000 mmol/l. Often, it is advantageous if the pharmaceutical agent contains a small excess (about 0.1 to 10 mol % relative to the diagnostically effective metal complex) of complexing agents. In a like manner, it can be advantageous for the pharmaceutical agent to contain small additions (about 0.1 to 10 mol % relative to the diagnostically effective metal complex) of metal complexes of weakly bound metals. In particular, sodium, calcium, magnesium and zinc complexes are suitable as additives in this regard. They can be used in the form of complexes with the complexing agents according to the invention, but also in the form of metal complexes with other complexing agents, such as DTPA, EDTA (ethylenediaminetetraacetic acid), TTHA (triethylenetetraaminehexaacetic acid) and derivatives of the latter. The resulting agents are then optionally sterilized. They are administered generally in a dose of about 1 to 300 ml on the basis of the diagnostic problem.

Suitable additives are, for example, physiologically harmless buffers (such as, e.g., tromethamine), small additions of complexing agents (such as, e.g., diethylenetriaminepentaacetic acid) or, if necessary, electrolytes, such as, e.g., sodium chloride or, if necessary, antioxidants, such as, e.g., ascorbic acid.

If suspensions or solutions of the agents according to the invention in water or physiological salt solution are desired for enteral administration or other purposes, they are mixed with one or more adjuvants usual in galenicals (e.g., methyl cellulose, lactose, mannitol), and/or surfactants (e.g., lecithins, Tweens®, Myrj®) and/or flavoring substances for taste correction (e.g., ethereal oils).

In principle, it is also possible to produce the diagnostic agents according to the invention even without isolating the complex salts. In each case, special care must be used to undertake the chelation, so that the salts and salt solutions according to the invention are practically free of noncomplexed metal ions having a toxic effect.

This can be assured, for example, with the help of color indicators, such as xylenol orange, by control titrations during the production process. The invention therefore also relates to a process for the production of complex compounds and their salts. A purification of the isolated complex salt remains as a final precaution.

The substances according to the invention meet the varied requirements which are to be imposed for contrast media in modern diagnosis. The compounds and agents produced from them are distinguished by a high absorption coefficient for X-rays, a high relaxivity, a good compatibility, which is necessary to maintain the noninvasive nature of the investigations, a high effectiveness, which is necessary to load the body with the smallest possible amounts of foreign substances, a good water solubility (this allows for the production of highly-concentrated solutions, as needed especially for use as X-ray contrast media. Thus, the volume load of the circulatory system is kept within reasonable limits), a low viscosity, low osmolality, advantageous excretion kinetics.

Further, the agents according to the invention exhibit not only a high stability in vitro, but also a surprisingly high stability in vivo, so that a release or an exchange of ions—toxic in themselves—not covalently bound to the complexes does not take place within the time in which the new contrast media are completely excreted again.

In addition to the high water solubility, which, surprisingly, was able to be increased to a range suitable for diagnostic radiology, the complex compounds according to the invention have a positive effect in diagnostic radiology in that they surprisingly permit investigations with shorter-wave X-ray radiation than that which is possible with conventional contrast media, by which the radiation exposure of the patient is clearly reduced, since, as is generally known, soft radiation of tissue is much more greatly absorbed than hard (R. Felix, Das Röntgenbild [The X-Ray Image]; Thieme Stuttgart 1980).

For use in diagnostic radiology, the complexes of the following metals according to the invention are especially suitable: gadolinium, terbium, dysprosium, holmium, erbium, ytterbium, lutetium, bismuth, lead and hafnium.

Because of the advantageous absorption properties of the contrast media according to the invention in the area of hard X-ray radiation, the agents are also especially suitable for digital subtraction techniques (which work with higher tube voltages).

It is further to be emphasized that the compounds according to the invention are distinguished by an improved heart/circulatory system compatibility in comparison with other complex compounds.

The surprisingly advantageous in vivo distribution behavior of the agents according to the invention is especially to be emphasized. This permits, for the first time, with a low dose for X-ray contrast media (about 0.1–1 mmol/kg of body weight), the production of X-ray pictures of high diagnostic informative value in the area of the liver, as well as of the bile ducts and the gallbladder, particularly in the case of use in computer tomography.

In addition to use in diagnostic radiology, the agents according to the invention, which contain in the complex a paramagnetic metal ion can also be used in NMR diagnosis. This dual nature opens up further fields of use. Thus, these agents according to the invention can be used advantageously if a combination of diagnostic radiology and NMR diagnosis is necessary for differentiated visualization and reliable determination of certain diseases. This is true, e.g., in the case of suspicion of recurrence after tumor operations or radiation therapy. In these cases, the patient is spared an additional load by double administration by using a contrast medium which is equally suitable for both techniques.

The complexing agents and their complexes according to the invention with weakly bound metals, (e.g., $Na^+$, $Ca^{2+}$, and $Mg^{2+}$ and $Zn^{2+}$) are, moreover, suitable to remove heavy metals from the body, for example, after a heavy metal poisoning. In particular, a detoxification of the liver is possible by the extrarenal excretion of the complexing agents and complexes according to the invention. The use of the compounds according to the invention for the production of agents for treating heavy metal poisonings, especially for treating heavy metal poisonings of the liver, are therefore also an object of the invention.

Further objects of the invention are characterized by the claims.

In general, it has been possible with the mentioned complex compounds to open up new possibilities in diagnostic and therapeutic medicine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

The following examples are used for a more detailed explanation of the objects of the invention without intending to be limiting.

Example 1

Dysprosium complex of the disodium salt of 3,6,9-triaza3,6,9-tris-(carboxymethyl)-2-(4-ethoxybenzyl)-undecanedioic acid a) N-Benzyl-tyrosine-tert-butyl ester 16.9 g (71.5 mmol) of tyrosine-tert-butyl ester and 8.33 g (78.6 mmol) of benzaldehyde are stirred in 50 ml of methanol for 3 hours at 24° C. and then mixed with 3.37 g (53.6 mmol) of sodium cyanoborohydride. After 24 hours of stirring at room temperature, the batch is adjusted to pH 2 by careful addition of semiconcentrated hydrochloric acid, then neutralized with concentrated aqueous sodium bicarbonate solution and, after substantial evaporation of methanol, it is shaken out with ethyl acetate. The organic phase is dried on anhydrous magnesium sulfate, filtered and concentrated by evaporation. The residue is chromatographed on silica gel with diethyl ether/hexane/triethylamine; the product-containing fractions are combined and concentrated by evaporation.

Yield: 15.7 g (67% of theory) of colorless oil.

Analysis (relative to solventless substance): Cld: C 73.37 H 7.70 N 4.28 O 14.66 Fnd: C 73.25 H 7.84 N 4.16 b) N-Benzyl-2-(4-hydroxybenzyl)-3-azaglutaric acid-di-tert-butyl ester 15.1 g (46.1 mmol) of N-benzyl-tyrosine-tert-butyl ester (Example a) is dissolved in 50 ml of tetrahydrofuran and mixed with 5 ml of water and 9.54 9 (69 mmol) of potassium carbonate. After instillation of 9.89 g (51 mmol) of bromoacetic acid-tert-butyl ester, it is stirred for two days at 65° C. After cooling, it is filtered, concentrated by evaporation in a vacuum and the residue is chromatographed on silica gel with diethyl ether/hexane/triethylamine. The product fractions are concentrated by evaporation in a vacuum and dried.

Yield: 14.9 g (73.3% of theory) of colorless oil.

Analysis (relative to solventless substance): Cld: C 74.33 H 8.22 N 3.94 O 13.50 Fnd: C 74.27 H 8.26 N 3.74 c) N-Benzyl-2-(4-ethoxybenzyl)-3-azaglutaric acid-di-tert-butyl ester 13.2 g (30 mmol) of N-benzyl-2-(4-hydroxybenzyl)-3-azaglutaric acid-di-tert-butyl ester (Example b) is dissolved in 50 ml of anhydrous N,N-dimethylformamide and mixed at 0° C. under argon with 1.31 g (33 mmol) of sodium hydride dispersion (60% in mineral oil). The batch is allowed to stir for 15 minutes, then 8.05 g (51.7 mmol) of ethyl iodide is added, the reaction temperature is allowed to increase to room temperature and it is stirred for another three hours. For working-up, the batch is taken up in toluene and shaken out several times against aqueous sodium bicarbonate solution. The organic phase is separated, dried on magnesium sulfate, filtered and concentrated by evaporation. The oily residue is chromatographed for purification on silica gel with hexane/diethyl ether/triethylamine. The product fractions are concentrated by evaporation in a vacuum and dried.

Yield: 12.7 g (90.3% of theory) of colorless oil.

Analysis (relative to solventless substance): Cld: C 71.61 H 8.37 N 2.98 O 17.03 Fnd: C 71.72 H 8.43 N 2.87 d) 2-(4-Ethoxybenzyl)-3-azaglutaric acid-di-tert-butyl ester 14.2 g (30.2 mmol) of the compound produced according to Example c) is dissolved in 75 ml of ethanol and, after the addition of 1.4 g of palladium (10%) on activated carbon under hydrogen atmosphere, it is hydrogenated at room temperature until hydrogen absorption is completed. After filtration and concentration by evaporation of the filtrate in a vacuum, a colorless oil is obtained.

Yield: 11.3 g (98.6% of theory)

Analysis (relative to solventless substance): Cld: C 66.46 H 8.77 N 3.69 O 21.08 Fnd: C 66.44 H 8.63 N 3.57 e) 3,6-Diaza-3-(tert-butoxycarbonylmethyl)-6-(2-hydroxyethyl)-octanedioic acid-di-tert-butyl ester 20.8 g (200 mmol) of N-(2-hydroxyethyl)-ethylenediamine is reacted with 128.55 g (660 mmol) of bromoacetic acid-tert-butyl ester and 124.4 g (900 mmol) of potassium carbonate in tetrahydrofuran/water analogously to Example b). After chromatographic purification, the title compound is obtained as colorless oil.

Yield: 82.7 g (92.6% of theory)

Analysis (relative to solventless substance): Cld: C 59.17 H 9.48 N 6.27 O 25.08 Fnd: C 59.24 H 9.60 N 6.13 f) 3,6-Diaza-3-(tert-butoxycarbonylmethyl)-6-(2-bromoethyl)-octanedioic acid-di-tert-butyl ester A solution of 33.8 g (75.8 mmol) of the compound described in Example e) and 22.9 g (87.1 mmol) of triphenylphosphine in 400 ml of dichloromethane is mixed at 0° C. in portions with 15.5 g (87.1 mmol) of N-bromosuccinimide and then stirred for 20 hours at room temperature. The solution is concentrated by evaporation and the residue is adsorptively precipitated with tert-butyl methyl ether. A precipitate develops, which is separated and washed with tert-butyl methyl ether. The combined filtrates are concentrated by evaporation and the residue is chromatographed on silica gel with hexane/diethyl ether. The concentration by evaporation of the product fractions produces a colorless oil.

Yield: 31.3 g (81.0% of theory)

Analysis (relative to solventless substance): Cld: C 51.87 H 8.11 Br 15.68 N 5.50 O 18.84 Fnd: C 51.69 H 8.20 Br 15.51 N 5.43 g) 3,6,9-Triaza-3,6,9-tris-(tert-butoxycarbonylmethyl)-2-(4-ethoxybenzyl)-undecanedioic acid-di-tert-butyl ester 7.59 g (20 mmol) of the compound produced according to Example d) and 11.2 g (22 mmol) of 3,6-diaza-3-(tert-butoxycarbonylmethyl)-6-(2-bromoethyl)-octanedioic acid-di-tert-butyl ester (Example f) are introduced into 45 ml of acetonitrile and mixed with 25 ml of 2N phosphate buffer solution (pH 8.0). The batch is stirred vigorously at room temperature for 22 hours, and the aqueous phosphate buffer phase is exchanged after 2 and 7 hours for fresh buffer solution. Then, the organic phase is concentrated by evaporation in a vacuum, and the residue is chromatographed on silica gel with hexane/ethyl acetate/triethylamine. The product-containing fractions are concentrated by evaporation in a vacuum.

Yield: 13.3 g (82.3% of theory) of colorless oil.

Analysis (relative to solventless substance): Cld: C 63.92 H 9.11 N 5.20 O 21.78 Fnd: C 64.07 H 9.20 N 5.08 h) 3,6,9-Triaza-3,6,9-tris-(carboxymethyl)-2-(4-ethoxybenzyl)-undecanedioic acid 12.6 g (15.6 mmol) of the pentaester described in Example g) is dissolved in 50 ml of methanol and mixed with 40 ml of 2 N sodium hydroxide solution. It is refluxed for three hours, the methanol is drawn off in a vacuum and stirred for another two hours at 60° C. Then, it is adjusted to pH 1 with concentrated hydrochloric acid, evaporated to dryness in a vacuum and the residue is adsorptively precipitated with isopropanol. After filtration and concentration by evaporation of the filtrate in a vacuum, a colorless solid is obtained.

Yield: 7.5 g (91.1% of theory)

Analysis (relative to anhydrous substance): Cld: C 52.37 H 6.31 N 7.97 O 33.36 Fnd: c 52.24 H 6.45 N 7.81 i) Dysprosium complex of disodium salt of 3,6,9-triaza3,6,9-tris-(carboxymethyl)-2-(4-ethoxybenzyl)-undecanedioic acid 6.9 g (13 mmol) of the penta acid described in Example h) is taken up in 30 ml of water, mixed with 2.42 g (6.5 mmol) of dysprosium oxide and stirred for eight hours at 85° C. Then, it is adjusted to pH 7.2 with diluted sodium hydroxide solution, filtered and the filtrate is freeze-dried.

Yield: 8.45 g (88.9% of theory) of colorless lyophilizate.

Analysis (relative to solventless substance): Cld: C 37.79 H 3.86 Dy 22.23 N 5.75 Na 6.29 O 24.08 Fnd: C 37.64 H 3.97 Dy 22.12 N 5.62 Na 6.04

Example 2

Ytterbium complex of the disodium salt of 3,6,9-triaza3,6,9-tris-(carboxymethyl)-2-(benzylmethyl)-undecanedioic acid a) 3,6,9-Triaza-2-(benzylmethyl)-nonanoic acid benzyl ester 13.4 g (50.0 mmol) of 2-oxo-4-phenylbutyric acid benzyl ester and 31.0 g (300 mmol) of diethylenetriamine are stirred in 200 ml of methanol for two hours at room temperature. Then, 0.95 g (25.0 mmol) of sodium borohydride is added in portions at 0° C. It is allowed to stir overnight, and the reaction mixture is gently concentrated by evaporation in a vacuum. The residue is dispersed between dichloromethane and water, the organic phase is dried on sodium sulfate, filtered and concentrated by evaporation. The residue is chromatographed on silica gel with use of dichloromethane/methanol/triethylamine (70:30:1) as mobile solvent. The fractions that contain the pure product are combined and concentrated by evaporation.

Yield: 13.5 g (75.9% of theory) of pale yellow oil.

Analysis (relative to solventless substance): Cld: C 70.96 H 8.22 N 11.82 O 9.00 Fnd: C 70.88 H 8.41 N 12.04 b) 3,6,9-Triaza-3,6,9-tris-(tert-butoxycarbonylmethyl)-2-(benzylmethyl)-undecanedioic acid-di-tert-butyl ester 6.91 g (50.0 mmol) of potassium carbonate is dissolved in 7 ml of water and mixed at 35° C. with 3.55 g (10.0 mmol) of triamine from Example a) in 50 ml of tetrahydrofuran. 9.75 g (50.0 mmol) of bromoacetic acid-tert-butyl ester is added drop by drop and the batch is stirred for three hours at 60° C. After 15 hours of stirring at room temperature, the reaction mixture is mixed with a little water and shaken out with ethyl acetate. The organic phase is dried on sodium sulfate, concentrated by evaporation, and the residue is chromatographed on silica gel (ethyl acetate/acetone). After the concentration by evaporation of the product-containing fractions, the pentaester is obtained as colorless oil.

Yield: 6.64 g (81.8% of theory)

Analysis (relative to solventless substance): Cld: C 66.56 H 8.56 N 5.18 O 19.70 Fnd: C 66.79 H 8.32 N 4.93 c) Ytterbium complex of the disodium salt of 3,6,9-triaza-3,6,9-tris-(carboxymethyl)-2-(benzylmethyl)-undecanedioic acid 15.6 g (19.2 mmol) of pentaester (from 3 batches corresponding to Example b)) is dissolved in 80 ml of methanol and reacted with 76.8 ml of 2N sodium hydroxide solution. It is stirred for five hours at 55° C., then the methanol is evaporated, water is added and it is evaporated again. It is taken up in water and adjusted to pH 1.9 with acid ion exchanger. After the exchanger is filtered out, the aqueous solution is mixed with 3.79 g (9.61 mmol) of ytterbium oxide and stirred at 95° C. After the complexing is completed, it is filtered, adjusted to pH 7.2, stirred with 0.2 g of activated carbon for ten minutes at 90° C., filtered again and the filtrate is freeze-dried.

Yield: 12.8 g (93.8% of theory) of colorless lyophilizate.

Analysis (relative to anhydrous substance): Cld: C 37.14 H 4.28 N 5.58 O 23.35 Yb 20.86 Na 6.10 Fnd: C 37.22 H 4.40 N 5.62 Yb 20.75 Na 6.03

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula I

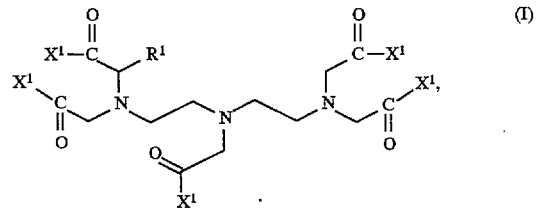

wherein $R^1$ is a radical of formula Ia

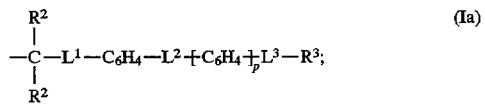

is 0 or 1;

$R^2$ is, in each case independently of one another, H or a branched or unbranched, saturated or unsaturated $C_1$–$C_6$ hydrocarbon radical;

$R^3$ is H, a carboxyl group, or a branched or unbranched, saturated or unsaturated $C_1$–$C_6$ hydrocarbon radical;

$L^1$ is a direct bond or $C_1$–$C_4$ alkylene;

$L^2$ and $L^3$ are, in each case independently of one another, a direct bond, an oxygen atom, a sulfur atom, $C_1$–$C_{10}$ alkylene, or $C_1$–$C_{10}$ alkylene interrupted by one to three oxygen atoms, one to three sulfur atoms or combinations thereof, wherein two or more heteroatoms are not directly connected with one another;

$X^1$ is, in each case independently of one another, O—$X^2$ or $N(R^4)R^5$;

$R^4$ and $R^5$ are, in each case independently of one another, H, $C_1$–$C_6$ alkyl or a $R^1$ group, or $R^4$ and $R^5$ together, with inclusion of the common amide nitrogen atom, form a four- to eight-membered ring, optionally containing 1 to 2 oxygen atoms and/or 1 to 2 carbonyl or sulfonyl groups;

$X^2$ is, in each case independently of one another, H or a metal ion equivalent of an element of atomic numbers 20–32, 39–51 or 57–83; or a physiologically acceptable salt thereof with inorganic and/or organic cations.

2. A compound according to claim 1, wherein $X^1$, in each case, is a O—$X^2$ group.

3. A compound according to claim 1, wherein one or two $X^1$ groups are $N(R^4)R^5$.

4. A compound according to claim 1, wherein at least two $X^2$ groups are metal ion equivalents of an element of atomic number 20–32, 39–51, or 57–83.

5. A compound according to claim 1, wherein all $X^2$ groups are H.

6. A compound according to claim 1, wherein sodium, calcium, magnesium, zinc, meglumine, glucosamine, arginine, ornithine, lysine and/or ethanolamine ions are present as physiologically compatible cations.

7. A compound according to claim 1, wherein $R^1$ is methoxybenzyl, ethoxybenzyl, propoxybenzyl, butoxybenzyl, pentoxybenzyl, ethoxy-ethoxybenzyl, 2-(2-ethoxy-ethoxy)ethoxybenzyl, 2-(methoxy)ethoxybenzyl, ((ethoxy)ethoxy)methoxybenzyl, benzyloxybenzyl, methylbenzyl, ethylbenzyl, propylbenzyl, butylbenzyl, pentylbenzyl or benzylbenzyl.

8. A compound according to claim 1, wherein said compound is:

3,6,9-triaza-3,6,9-tris-(carboxymethyl)-2-(4-ethoxybenzyl)-undecanedioic acid or a physiologically acceptable salt thereof;

3,6,9-triaza-3,6,9-tris-(carboxymethyl)-2-(benzylmethyl)-undecanedioic acid or a physiologically acceptable salt thereof;

dysprosium complex of 3,6,9-triaza-3,6,9-tris-(carboxymethyl)-2-(4-ethoxybenzyl)-undecanedioic acid or a physiologically acceptable salt thereof; or ytterbium complex of 3,6,9-triaza-3,6,9-tris-carboxymethyl)-2-(benzylmethyl)-undecanedioic acid or a physiologically acceptable salt thereof.

9. A compound according to claim 1, wherein said compound contains a paramagnetic metal.

10. A compound according to claim 1, wherein said compound contains a radioactive metal.

11. A compound according to claim 1, wherein said compound contains a metal of the lanthanide series.

12. A compound according to claim 11, wherein said metal is gadolinium, dysprosium, holmium, erbium, terbium or ytterbium.

13. A compound according to claim 1, wherein said compound contains bismuth, lead or hafnium.

14. A compound according to claim 9, wherein said paramagnetic metal is manganese or iron.

15. A compound according to claim 10, wherein said metal is gallium, indium or technetium.

16. A compound according to claim 1, wherein said compound contains calcium or zinc.

17. A pharmaceutical agent comprising at least one physiologically compatible compound according to claim 1, a physiologically acceptable carrier and, optionally, at least galenic additives.

18. In a method of diagnostic radiology comprising administering a diagnostic agent, the improvement wherein said agent contains at least one physiologically compatible compound according to claim 1, wherein said compound is a chelate complex.

19. In a method of NMR diagnosis comprising administering a diagnostic agent, the improvement wherein said agent contains at least one physiologically compatible compound according to claim 1, wherein said compound is a chelate complex containing a paramagnetic metal ion.

20. In a method of radiodiagnosis comprising administering a diagnostic agent, the improvement wherein said agent contains at least one physiologically compatible compound according to claim 1, wherein said compound is a chelate complex of a radioisotope.

21. In a method of diagnostic radiology, NMR diagnosis and/or radiodiagnosis comprising administering a diagnostic agent, the improvement wherein said agent contains at least one physiologically compatible compound according to claim 1, wherein said compound is a chelate complex, and imaging of the liver, gallbladder and/or bile ducts is performed.

22. A method according to claim 21, wherein diagnostic imaging of the liver, the gallbladder and/or the bile ducts is performed by computer tomography.

23. In a method of radiotherapy comprising administering a radiotherapeutic agent, the improvement wherein said agent contains at least one physiologically compatible compound according to claim 1, wherein said compound is a chelate complex containing a radioisotope.

24. In a method of removing undesirable heavy metals from an organism, comprising administering an agent, the improvement wherein said agent contains at least one physiologically compatible compound according to claim 1.

25. A method according to claim 24, wherein undesirable heavy metals are removed from the liver.

26. A compound according to claim 1, wherein at least two $X^2$ groups are metal ion equivalents of an element of atomic numbers 57–83.

27. A pharmaceutical agent according to claim 17, wherein said compound is a chelate complex present in a concentration of 1–1500 mmol/l.

28. A compound according to claim 1, wherein $R^1$ is 4-ethoxy or benzylmethyl.

29. A compound according to claim 11, wherein said metal is dysprosium or ytterbium.

* * * * *